(12) United States Patent
Gourgouliatos et al.

(10) Patent No.: US 8,206,426 B2
(45) Date of Patent: Jun. 26, 2012

(54) LIGHT SOURCE AND FIBER OPTIC BRUSH FOR LIGHT DELIVERY

(75) Inventors: Zafirios Gourgouliatos, Los Angeles, CA (US); David Chang, Encino, CA (US)

(73) Assignee: Lerner Medical Devices, Inc., Los Angeles, CA (US)

( * ) Notice: Subject to any disclaimer, the term of this patent is extended or adjusted under 35 U.S.C. 154(b) by 1199 days.

(21) Appl. No.: 12/014,450

(22) Filed: Jan. 15, 2008

(65) Prior Publication Data

US 2008/0172112 A1 Jul. 17, 2008

Related U.S. Application Data

(60) Provisional application No. 60/880,812, filed on Jan. 17, 2007, provisional application No. 60/880,883, filed on Jan. 17, 2007, provisional application No. 60/880,813, filed on Jan. 17, 2007, provisional application No. 60/880,887, filed on Jan. 17, 2007.

(51) Int. Cl.
*A61N 5/06* (2006.01)

(52) U.S. Cl. ............... 607/94; 607/88; 607/89; 604/289; 604/290

(58) Field of Classification Search ............... 607/88–91, 607/93, 94; 385/100, 109, 115, 116, 118, 385/123
See application file for complete search history.

(56) References Cited

U.S. PATENT DOCUMENTS

| | | | |
|---|---|---|---|
| 2,397,757 A | 4/1946 | Schwedersky | |
| 4,423,531 A | 1/1984 | Wall | |
| 4,520,816 A | 6/1985 | Schacher et al. | |
| 4,558,700 A | 12/1985 | Mutzhas | |
| 5,300,097 A * | 4/1994 | Lerner et al. | 607/93 |
| 6,074,411 A | 6/2000 | Lai et al. | |
| 6,254,625 B1 | 7/2001 | Rosenthal et al. | |
| 6,270,492 B1 | 8/2001 | Sinofsky | |
| 6,447,537 B1 * | 9/2002 | Hartman | 607/94 |
| 6,494,899 B1 | 12/2002 | Griffin et al. | |
| 2002/0133144 A1 | 9/2002 | Chan et al. | |
| 2003/0057385 A1 | 3/2003 | Magne et al. | |
| 2003/0076281 A1 | 4/2003 | Morgan et al. | |

(Continued)

OTHER PUBLICATIONS

Taneja, A. et al., "Broad-band UVB fiber-optic comb for the treatment of scalp psoriasis: a pilot study", *International Journal of Dermatology*, vol. 43, pp. 462-467, 2004.

(Continued)

*Primary Examiner* — Melanie Hand
(74) *Attorney, Agent, or Firm* — Mark G. Lappin; Elizabeth E. Powers

(57) ABSTRACT

A phototherapy apparatus is disclosed including: a handpiece including a body member and a grip; a plurality of elongated light transmitting elements, each of the elements extending between a proximal end enclosed within the body member and a distal end located outside of and distal to the body member; an ultraviolet light source; a light collection element; and one or more optical coupling elements. The proximal ends of the light transmitting elements are located in close proximity to each other The light collection element is configured to collect at least a portion of the light emitted from the light source. The one or more optical coupling elements are configured to direct at least a portion of the collected light to the proximal ends of the light transmitting elements to couple at least portion of the collected light into the light transmitting elements The light coupled into each of the light transmitting elements is transmitted along the element and emitted from the distal end.

42 Claims, 14 Drawing Sheets

U.S. PATENT DOCUMENTS

| | | |
|---|---|---|
| 2003/0233138 A1 | 12/2003 | Spooner |
| 2005/0135102 A1 | 6/2005 | Gardiner et al. |
| 2005/0143793 A1* | 6/2005 | Korman et al. ............... 607/94 |
| 2005/0154382 A1 | 7/2005 | Altshuler et al. |
| 2005/0267452 A1 | 12/2005 | Farr et al. |
| 2006/0178712 A1 | 8/2006 | Carullo, Jr. et al. |
| 2006/0200116 A1 | 9/2006 | Ferren et al. |
| 2006/0257083 A1* | 11/2006 | Rasmussen ............... 385/115 |
| 2006/0276862 A1* | 12/2006 | Irwin ............................ 607/94 |

OTHER PUBLICATIONS

PCT International Search Report (PCT/US08/00495); Date of mailing Jun. 18, 2008; 1 page.

PCT International Search Report (PCT/US08/00499); Date of mailing Jul. 7, 2008; 1 page.

PCT International Search Report (PCT/US08/00545); Date of mailing Jul. 11, 2008; 1 page.

* cited by examiner

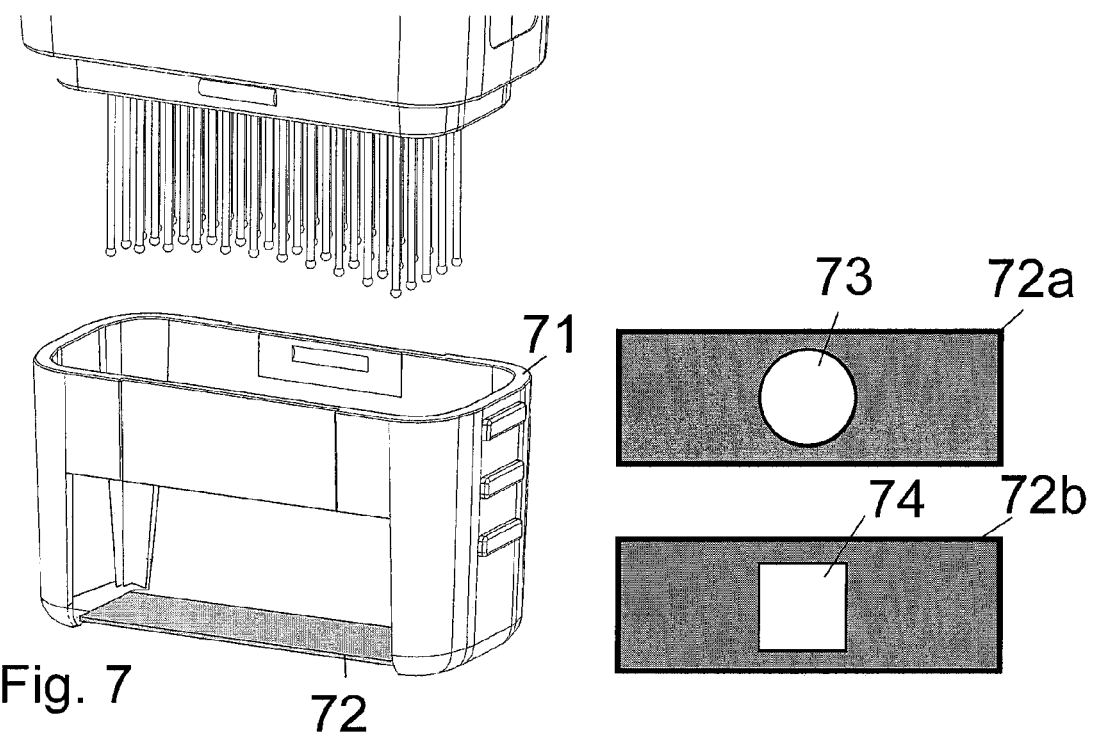

| Type | Typical UVB MED of unexposed skin (mJ/cm²) | Recommended Start Dose @ 2 MEDs (mJ/cm²) | Recommended End Dose* (mJ/cm²) |
|---|---|---|---|
| I | 45 | 90 | 240-360 |
| II | 75 | 150 | 600-750 |
| III | 90 | 180 | 720-950 |
| IV | 120 | 240 | 900-1,100 |
| V | 150 | 300 | 1,000-1,200 |
| VI | 240 | 480 | 1,200-1,400 |

*Depending on patient tolerance.

Treatment doses for Wavelength Optimized UV-B.

Fig. 12

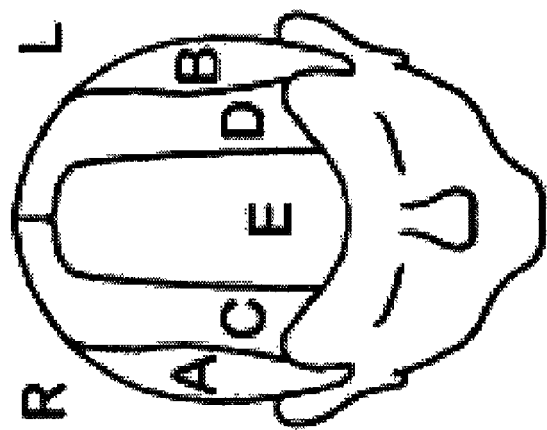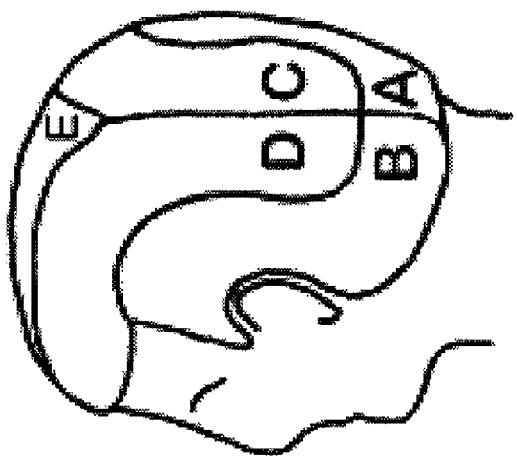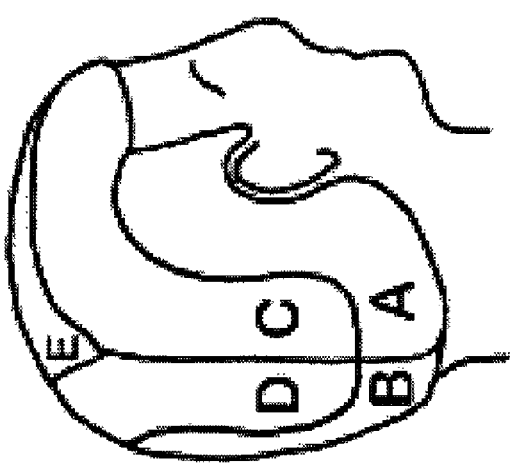
Fig. 13

LIGHT SOURCE AND FIBER OPTIC BRUSH FOR LIGHT DELIVERY

CROSS REFERENCE TO RELATED APPLICATIONS

The present application claims priority from U.S. Provision Application Ser. No. 60/880,883, U.S. Provisional Application Ser. No. 60/880,812, U.S. Provisional Application Ser. No. 60/880,813, U.S. Provisional Application Ser. No. 60/880,887, each filed Jan. 17, 2007, and each of which is incorporated by reference herein in its entirety.

BACKGROUND

This disclosure relates to phototherapy treatments for inflammatory diseases of the skin located on the scalp and other parts of the body covered by hair and more specifically to treatment of ultraviolet light-responding dermatoses.

Inflammatory diseases of the skin affect a large portion of the population resulting in significant morbidity. Psoriasis, for example, affects at least 1% of the population. This disease involves an abnormally fast rate of cell proliferation in the basal layer of the epidermis giving rise to red, scaly plaques and bleeding when traumatized (the "Auspitz sign"). Past methods of treatment of skin psoriasis include the application of tars, salicylic acid, steroids, ultraviolet light (phototherapy), and a combination of ultraviolet light, used in conjunction with photoactive compounds (photochemotherapy).

Photochemotherapy involves treatment with ultraviolet radiation of an affected area in combination with a topically or systemically applied medicament that sensitizes the skin to ultraviolet radiation (e.g., psoralen). Typically ultraviolet-A (UV-A) light (so-called long wave UV light) having wavelengths from 310 to 440 nm is used for this purpose. Unfortunately, successful treatment requires that UV radiation must be applied until an erythema (sunburn) is created. In some cases, the eyes of patients systemic undergoing psoralen and topical UV treatment may be sensitized to sunlight for several hours after treatment. In addition, some patients find the medicament difficult to tolerate. Furthermore, this therapy requires 20-25 radiation sessions which result in darkening of the pigmentation of the skin. In addition, treatment of scalp psoriasis in particular has been limited by two other problems. First, patients are reluctant to apply medications regularly which must remain on their scalps for hours at a time. Second, light from conventional treatment devices does not effectively penetrate hair covering the scalp.

Phototherapy involves simply UV irradiation of the affected area. For example, psoriasis has been treated with ultraviolet-B (UV-B) light having wavelengths from 290-320 nm. Other skin diseases which have been treated successfully with ultraviolet light include eczema, mycosis fungoides, and lichen planus. In addition, ultraviolet light may have a role in the treatment of seborrheic dermatitis.

Phototherapeutic methods have included the use of mercury vapor high pressure radiation devices and those UV sources having varying spectral distribution. For example, UV-B lamps such as devices which produce radiation from a metal halide or mercury vapor source and which filters the emitted UV light with colored glass have been used (see e.g., U.S. Pat. No. 4,558,700). These devices emit UV in the range of 270-365 nm (mostly 270-315 nm), and cause erythema. Devices which emit wavelengths of 320-330 nm and greater have also been used for so-called super-high-intensive phototherapy (SHIP).

A prior art device is adapted to deliver UV radiation to the scalp. That device is a hair brush for purportedly promoting the healthy flow of blood to the glands and roots of hair, and for promoting vitamin D production. The hair brush has an internal UV radiation source and UV radiation-transmitting bristles of a material other than a fiber optic material (Schwedersky, U.S. Pat. No. 2,397,757). Because the bristles of this device are rigid and pointed, its use on psoriasis-affected skin heightens the incidence of the Auspitz sign, and thus is contra-indicated for treatment of psoriasis.

Lerner et al., U.S. Pat. No. 5,300,097 describes a light delivery apparatus which includes a body member and a plurality of optical fibers extending therefrom. The optical fibers are adapted to couple the light generated at the optical source from the proximal tips of the optical fibers, through the fibers, and to their distal tips. Each fiber has a proximal tip affixed to the body member and a distal tip at the end opposite the proximal tip. Also described are methods of treating inflammatory dermatoses using the light delivery apparatus. The method includes contacting a region of the body afflicted with a dermatosis with the distal tips of the device such that UV light emanating therefrom is incident on the contacted region. In some cases, the method includes the additional step of, prior to the contacting step, applying a medicant or lubricant to the region to be treated.

Therefore, a need exists for a simple device and method useful for treating affected areas of the skin, particularly those hair-covered regions such as the scalp.

Existing devices have limitations that the light source and delivery are separate requiring light cable to connect, adding to cost and hindering use facility. In addition, in the integrated devices, the proposed schemes of coupling light have efficiency limitations because of the small area of the fibers that transmit the light to the target.

SUMMARY

The present disclosure describes a phototherapy delivery device for effective treatment of inflammatory dermatoses such as psoriasis in hair bearing areas of the skin such as the scalp and scrotum. This device includes of a fiberoptic based light delivery apparatus.

In light of the above, it is an object of this disclosure to provide a therapeutic device for the delivery of UV irradiation directly to an area of the body afflicted with psoriasis or other related dermatoses.

Yet another object is to provide a method of treating psoriasis and related dermatoses which is easy to administer, rapid, and which minimizes unpleasant side effects such as erythema, pigmentation darkening, and the Auspitz sign.

An additional object of the disclosure is to provide a method of treating psoriasis which minimizes the therapeutic sessions required to result in relatively rapid healing.

These and other objects of the disclosure will be apparent from the drawing description, and claims that follow.

In one aspect, a phototherapy apparatus is disclosed including: a handpiece including a body member and a grip; a plurality of elongated light transmitting elements, each of the elements extending between a proximal end enclosed within the body member and a distal end located outside of and distal to the body member; an ultraviolet light source; a light collection element; and one or more optical coupling elements. The proximal ends of the light transmitting elements are located in close proximity to each other The light collection element is configured to collect at least a portion of the light emitted from the light source. The one or more optical coupling elements are configured to direct at least a portion of the collected light to the proximal ends of the light transmitting elements to couple at least portion of the collected light into the light transmitting elements The light coupled into each of the light transmitting elements is transmitted along the element and emitted from the distal end.

In some embodiments, the light transmitting elements each include an optical fiber.

In some embodiments, the light transmitting elements are detachably affixed to the body member. Some such embodiments include a support plate adapted to be detachably received by the body member and to support the elongated light transmitting elements.

Each of the elongated light transmitting elements extend through the support element from a side of the support element proximal the body member to a side of the support element distal the body member. In some embodiments, the light transmitting elements and support plate are autoclavable.

In some embodiments, the proximal ends of the light transmitting elements include a linear array of fibers, the array having an entrance face included of the tips of the proximal ends. The one or more optical coupling elements are configured to direct light to the entrance face. Some such embodiments include a cylindrical lens disposed in front of the entrance face of the linear array of fibers and configured to concentrate light directed to the proximal ends of the light transmitting elements onto the entrance face.

In some embodiments, the proximal ends of the light transmitting elements include a fiber bundle, the bundle having an entrance face included of the tips of the proximal ends.

The one or more optical coupling elements are configured to direct light to the entrance face. Some such embodiments include a plurality of light concentrating elements disposed in front of the entrance face of the fiber bundle, the concentrating elements configured to concentrate light directed to the proximal ends of the light transmitting elements onto the entrance face. In some embodiments, the fibers of the fiber bundle are fused in proximity to the entrance face.

In some embodiments, the light collecting element includes one of the group of: an ellipsoidal reflector, a parabolic reflector. In some embodiments, the reflector includes a wavelength selective coating adapted to reflect radiation with wavelengths within a desired range and transmit radiation with wavelengths within a desired range, the desired range being within the ultraviolet range.

Some embodiments include one or more filter elements configured to filter out at least a portion of the light from the source having undesired wavelengths. In some embodiments, the filter element includes a dichroic mirror positioned to direct at least a portion of the collected light having undesired wavelengths away from the proximal ends of the light transmitting elements.

In some embodiments, the one or more optical coupling elements include a lens configured to focus light from the light collecting element to the proximal ends of the light transmitting elements.

Some embodiments include one or more shutters adapted to selectively block light directed to the proximal ends of the light transmitting elements.

In some embodiments, the portion of light coupled into the light transmitting elements includes substantially only ultraviolet light. In some embodiments, the portion of light coupled into the light transmitting elements has a spectral range within the range of 280 nm to 320 nm, within the range of 308 nm to 320 nm, or within the range of 320 nm to 380 nm.

In some embodiments, the light source includes at least one of the group of: a lamp, a laser, an excimer laser, a diode laser, a light emitting diode, an excimer gas discharge lamp.

In some embodiments, the distal ends of the light transmitting elements are arranged in an array. In some embodiments, the array is a two dimensional array. In some embodiments, tips of the distal ends of the light transmitting elements are located at positions in space having a locus characterized by a curved surface or arc. In some embodiments, the curved surface or arc includes one of the group of: a circular arc, a parabolic arc, and ellipsoidal arc, a cylindrical segment, a spherical segment, a toroidal segment. In some embodiments, the curved surface or arc has an associated radius or radii of curvature within the range of about 2 inches to about 6 inches. In some embodiments, the locus is adapted to substantially conform to the shape of a human scalp In some embodiments, the array is arranged to provide substantially uniform fluence of light emitted from the distal ends of the light transmission elements at an area of a treatment surface.

In some embodiments, the distal end of one or more of the light transmitting elements includes a bulbous tip included of a light emitting spherical segment. The spherical segment may have a radius of curvature within the range of about 0.25 mm to about 3.0 mm.

In some embodiments, the distal end of one or more of the light transmitting elements includes a rounded tip. In some embodiments, the rounded tip may have a radius of curvature within the range of about 0.25 mm to about 3.0 mm.

In some embodiments, one or more optical fibers include an inner core surrounded by an outer cladding, the inner core having a radius within the range of about 0.1 mm to about 3 mm.

Some embodiments include a control unit in communication with one or more of: the light source, collecting element, or the one or more optical coupling elements. The control unit configured to selectively adjust the duration or intensity of light emitted from the distal ends of the light transmitting elements. In some embodiments, the control unit is in communication with a power supply, and the control unit configured to control the power supplied to the light source to adjust the duration or intensity of light coupled into the light transmitting elements. Some embodiments include a dosimetry sensor adapted to, during operation, provide to the control unit information indicative of a dose of treatment light directed from the light transmitting elements to a treatment surface.

In some embodiments, the control unit is configured to selectively adjust the duration or intensity of light coupled into the light transmitting elements based on the information.

Some embodiments include a power supply. The power supply may be enclosed within the body element.

In some embodiments, the body element is substantially opaque to ultraviolet light.

Some embodiments include a sensor adapted to sense the proximity or contact of the distal end of one or more of the elongated light transmitting elements to a treatment surface. The sensor may be in communication with the control unit, and the control unit is configured to inhibit emission of light from the source when the sensor does not indicate proximity or contact of the distal end of one or more of the elongated light transmitting elements to the treatment surface.

In another aspect, a method of treating an area of skin affected by skin disease is disclosed including providing an effective dose of treatment light to the affected area from a phototherapy device of any of the types described above.

In some embodiments, the treatment light includes ultraviolet light.

In some embodiments, providing treatment light includes bringing the distal ends of the light transmitting elements into proximity or contact with the affected area.

In some embodiments, providing treatment light includes, while maintaining distal ends of the light transmitting elements into proximity or contact with the affected area, moving the distal ends across the affected area to provide at least one minimal erythema dose of treatment light to substantially the entire the affected area.

In some embodiments, at least a portion of the affected area is a hair bearing region, and moving the distal ends across the affected area includes combing the distal ends through the hair.

It is to be understood that, as used herein, skin disease includes inflammatory skin disease such as psoriasis, vitiligo, pigmentation loss, and other disorders.

Various embodiments may include any of the above described features, alone or in any combination. These and other features will be more fully appreciated with reference to the following detailed description which is to be read in conjunction with the attached drawings.

DESCRIPTION OF THE DRAWINGS

The foregoing and other objects of this disclosure, the various features thereof, may be more fully understood from the following description, when read together with the accompanying drawings in which:

FIG. 2a shows a system based on an ellipsoidal reflector and FIG. 2b shows a system based on an reflector with a parabolic profile.

FIG. 7 shows a diffuser attachment for spot treatment;

FIG. 12 is an exemplary phototherapy dosage table;

FIG. 13 is an illustration showing the division of a human scalp into treatment areas.

Like reference numerals refer to like elements throughout the figures.

DESCRIPTION

Figure 1:
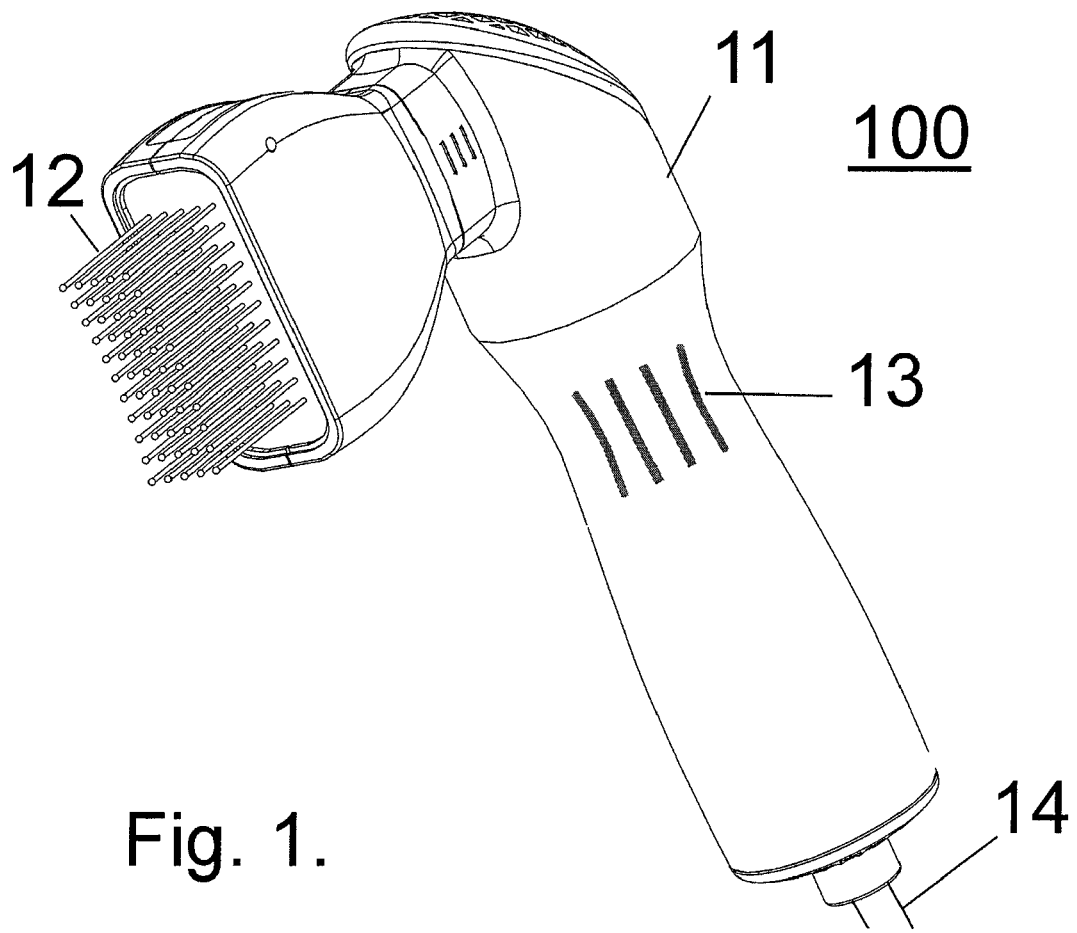
FIG. 1 is a perspective view showing an exemplary of the integrated light source and fiberoptic light delivery device.
Figure 2A:
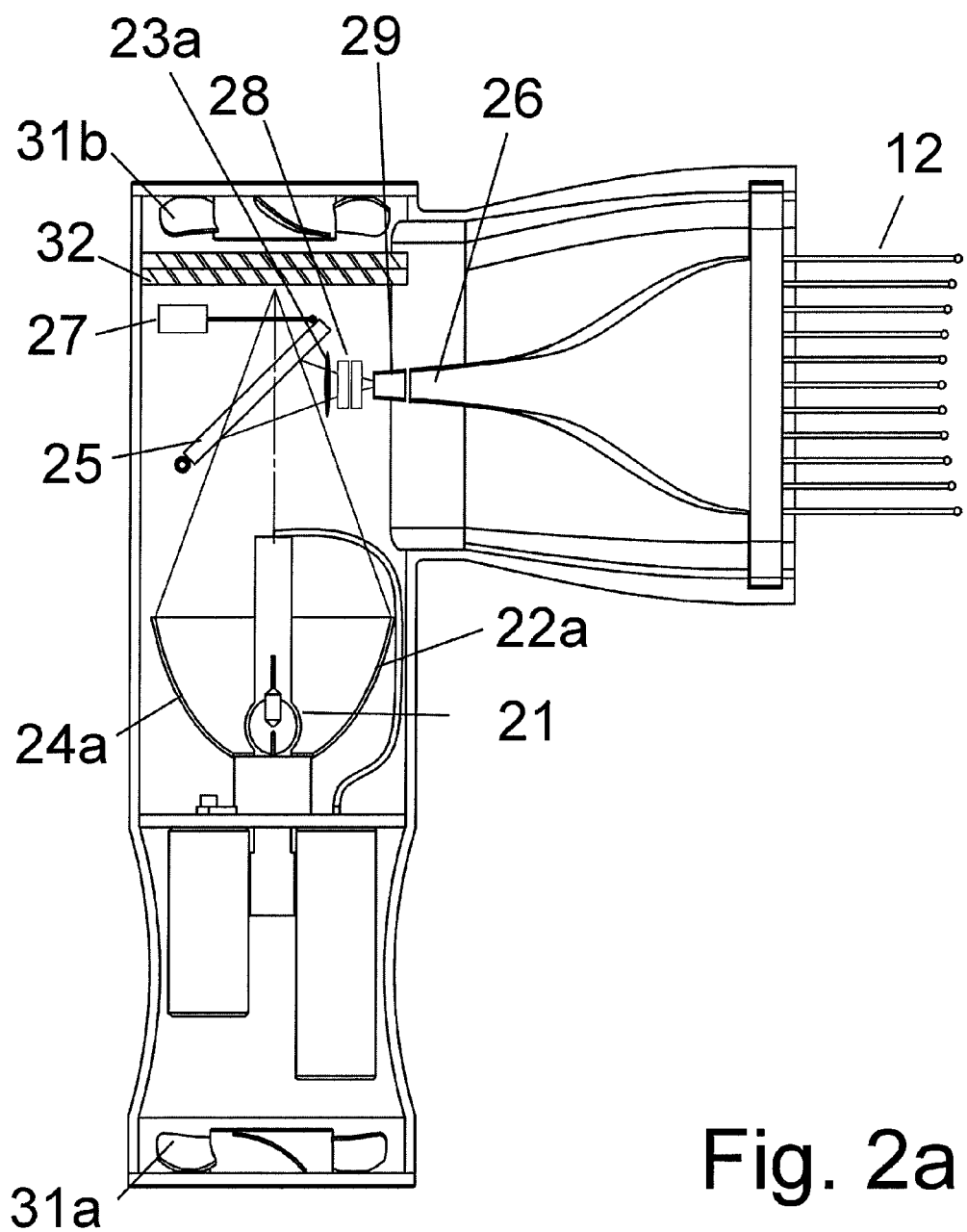
FIGS. 2a and 2b shows two arrangements of the optical components.
Figure 2B:
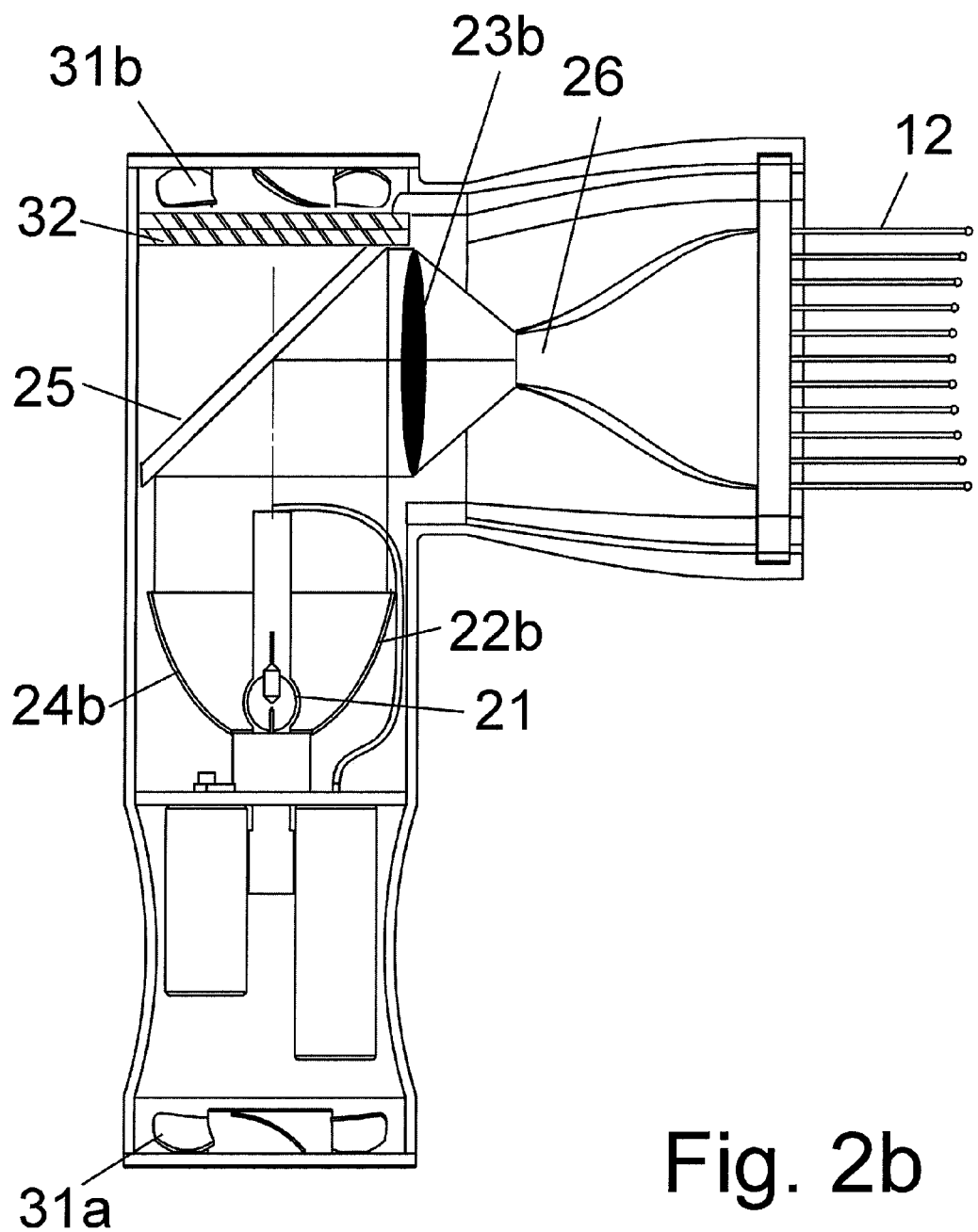

Therapeutic device 100 is shown in FIG. 1, and includes a light delivery apparatus including body member 11 and a plurality of light transporting elements, such as optical fibers 12 extending therefrom. Body member 11 encloses the light producing, filtering, beam shaping and coupling elements (shown in FIGS. 2a and 2b) as well as power supply, electrical and electronic elements to power the lamp and safety devices. The lower end of the body can form a grip 13 for comfortable handling. The body can be connected to an external source of electrical power with an electrical cable 14 to receive said power. The external electrical source can also incorporate control mechanisms for the device. The body can have alternative configurations so that it embodies of provides for the attachment of handles for more security and comfort of handling during use.

Preferably, body member 11 has substantially no UV-transferring abilities, and is formed of a molded resinous material, such as plastic, rubber, and the like.

The light for the treatment can be provided by a short arc discharge lamp 21 (FIGS. 2a and 2b) but also by a compact laser, excimer laser, excimer gas discharge lamp, Light Emitting Diode (LED), or lamp of other type. The lamp can be placed into a concave reflector, such an ellipsoidal reflector 22a that concentrates the light to a small spot or in a parabolic reflector 22b that creates a parallel or almost parallel beam which is concentrated into a small area with a lens 23b. The lens can be of various materials, size, shape and focal length. The reflector preferably has a metal or dichroic coating 24a, 24b to allow the unneeded spectrum of light to pass through its surface and reflect light mainly in the spectrum needed for treatment. Such spectrum can be ultraviolet b light 280 to 320 nm or a subset of this spectrum.

The light can be reflected by a mirror 25 that is at an angle to the axis of the system. In the embodiment shown the angle of the mirror to the beam is 45 degrees but it can be any other angle from 20 to 70 degrees. This mirror may have a metal or dichroic coating, preferably UV-enhanced to reflect the light into the entrance of a fiber bundle 26 where the fibers 12 are brought together. Said mirror can be flat but also curved to work in combination with the other optical elements for light collection. In the path of the light there can alternatively be a shutter 27 (FIG. 10) and a set of filters 28. The filters can be alternatively fitted on the shutter.

In front of the fiber bundle 26, light concentrating elements 29 (FIG. 2a) can be placed such as hollow or solid made out of transparent material, in the shape of cones, cylinders or other manifold geometry transparent optics.

In an alternative embodiment, the light is concentrated into a line for fiber arranged also into a line at the receiving end. This light concentration is achieved with the placement of a cylindrical lens 23a. Such lens affects the focus of light in one axis.

The body member 11 can have indentations and/or protrusions for holding the components. In addition it can have grooves and or holes to allow for passage of air to cool the lamp and reflector. In addition it can provide space for cooling fans 31a and 31b for forced air circulation. A light blocking louver 32 can be placed in front of the holes or close to the interior side of the fan to block light from exiting through these holes.

Figure 3:
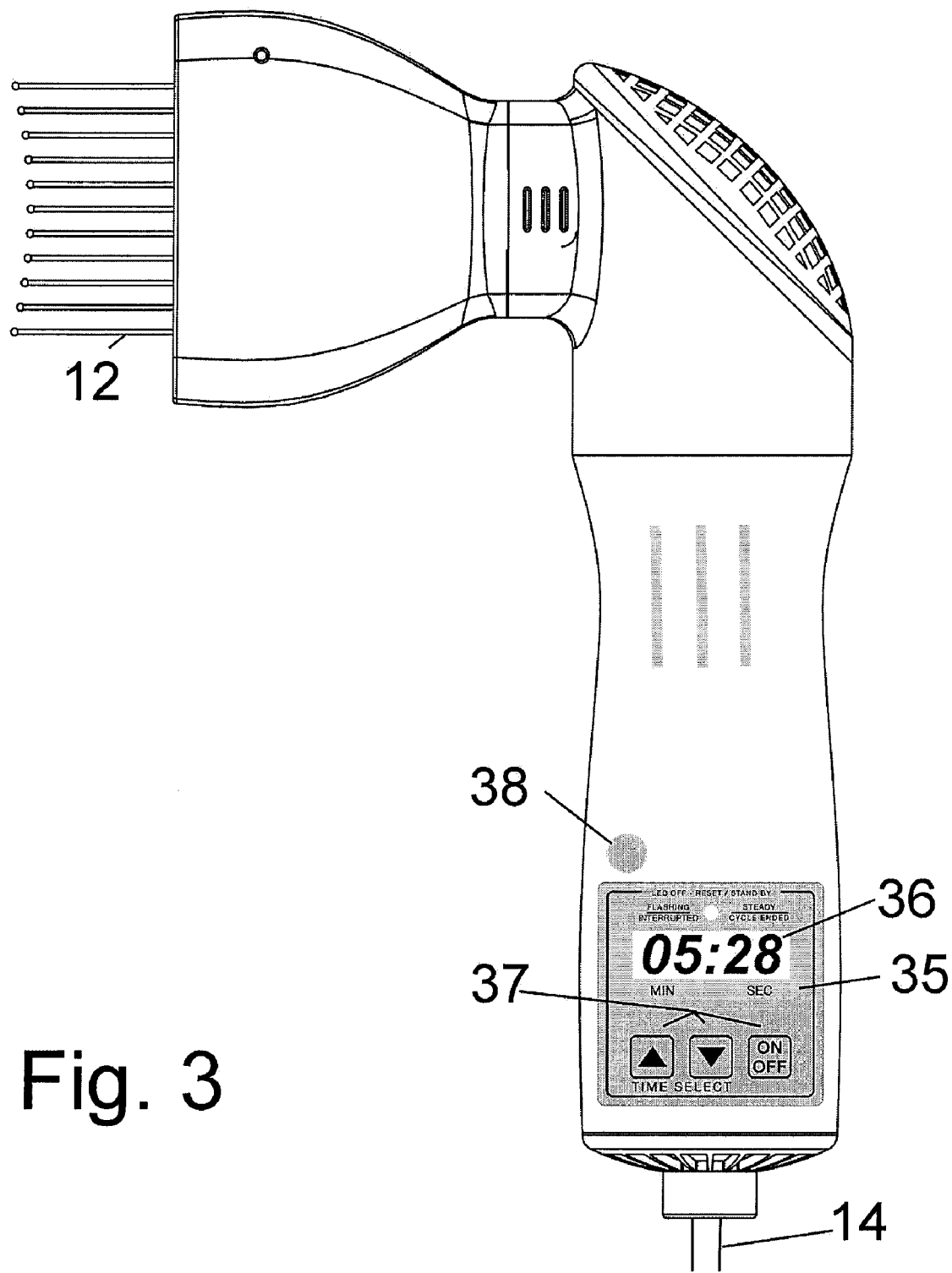
FIG. 3 shows an alternative embodiment of the device of FIG. 1 where a status indicator, control buttons and an auditory signal transducer is included in the assembly.

The treatment parameters such as exposure time and intensity need to be set before use of this Fiberoptic Brush. Typically the controls that set the treatment are located on the light source. In the embodiment of FIG. 3 the controls are embodied in the device body for convenience to the user. Specifically, therapeutic device body member 11 can include control module 35 with display 36 and input elements 37 on body member surface, auditory signal transducer 38 for operator warnings. Communication with the electrical source (if the electrical source is not internal) can be achieved either by wire 14, or fiber optic connection.

Figure 4:
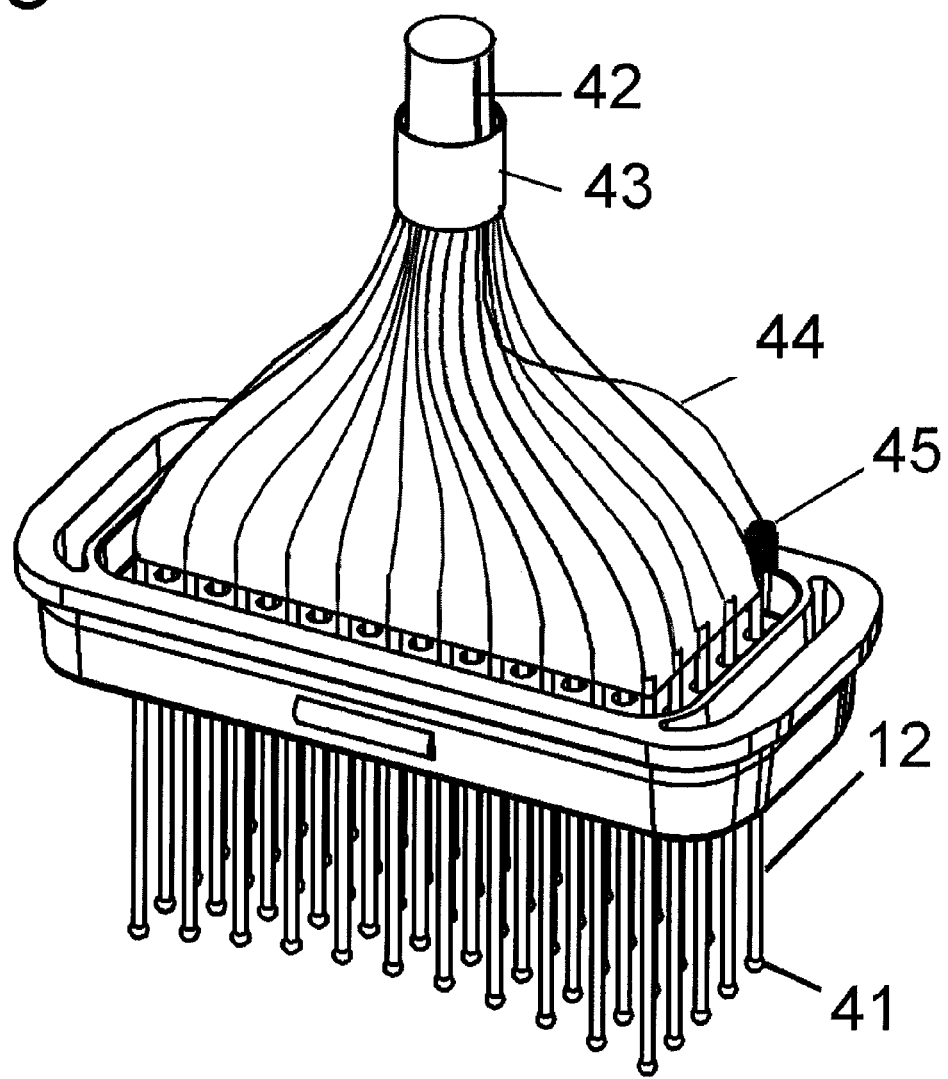
FIG. 4 shows the fiber optics arrangement, including a feature for light feedback
Figure 5:
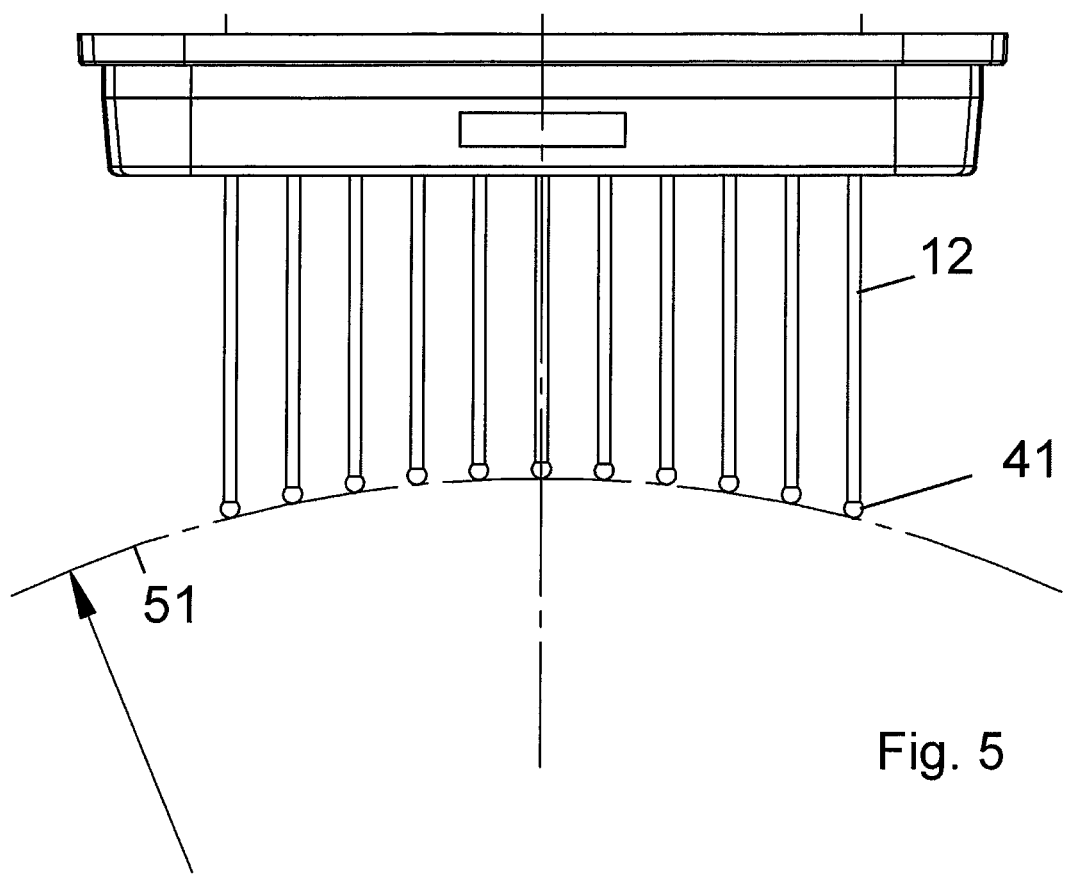
FIG. 5 shows a detail of the fiber tip arrangement.

The elements to transport the light from the lamp to the patient can be fiber optics distally arranged in a grid or rows and columns. In FIG. 4 an embodiment of 5 rows and 11 columns is shown. The light transporting elements can also be arranged in a single line 51 as shown in. FIG. 5, or multiple rows. The length of the light transporting elements is reasonable for combing action while maintaining skin contact and is typically in the range of 0.5 to 2.5 inches. The distance between each of the light transporting elements is preferably in the range of 0.05 to 0.5 inches. The grid depicted is square but it can also be a slanted rectangular, zigzag, honeycomb or semi random for better spreading of light delivery when combing. The size of the outline of the grid is preferably in the range of 0.5 to 2 inches in width and 0.5 to 5 inches in length. When the fiber arrangement is in single line, the length of the profile can be between 0.5 and 5 inches.

The light transporting elements 12 can be single optical fibers with diameter 400 um to 2 mm (preferably 600 um for array, 800 um for in line) or fiber bundles. Central core is composed of a material which is capable of transmitting UV irradiation, such as fused silica, solarization resistant fused silica, plastic, or glass. The cladding can be a lower refractive index polymer cladding (giving a Numerical Aperture (NA) 0.2 to 0.51, typically 0.39 NA). The outer jacket can be Teflon, nylon or formable resinous material, such as plastic, silicone, rubber, and the like. Cladding material can also be a lower refractive index glass or fused silica cladding (0.1 to 0.31 NA, typically 0.22 NA). Of course, in some alternative embodiment, the light transmitting element can be hollow or filled tubes with internal diameter of 0.1-3 mm with smooth, polished, UV reflecting internal surfaces. The tubes can be cylindrical or conical or a combination of these two surfaces. Fibers 12 are hardy and ideally autoclavable or able to be gas sterilized.

The distal tips 41 of the light transporting elements can be arranged on a straight line if a single row or on a plane if an array. They can also be preferably arranged on a curved line 51 (shown on FIG. 5) or curved surface to match the shape of the scalp. The curved line can potentially resemble an arc of a circle, parabola, ellipsoid or other curved line. If an arc of a circle, the radius of the circle can be in the range of 2 to 6 inches to accommodate different scull sizes. In the case of an array, the surface can be part of a cylinder, sphere, toroidal, ellipsoidal or other curved surface. If a cylindrical surface is chosen, the radius of the cylinder can be in the range of 2 to 6 inches to accommodate different scull sizes. In a similar manner if a spherical or toroidal surface is chosen, the radius or radii can be in the range of 2 to 6 inches.

Distal tips 41 (FIG. 4, FIG. 5) of fibers 12 are spherical segments. They can be made out of a UV light transmitting spherical element or can be just rounded tips of the fiber. The distal tips have a radius of curvature in the range of about 0.25-3.0 mm, to ensure that minimal damage is done to the skin during use. They should be smooth and small enough to easily be moved through the hair in brush-like fashion. The Ball tips can be made of epoxy substances, molded plastic, fused silica, sapphire, or other materials that allow light transmission.

For improved coupling to the lamp and optical system the fibers need to be brought together at the receiving end 42 and form a fiberoptic bundle. In order for the fibers to be mechanically held together a ring 43 is preferentially placed where the fibers are brought together. For light loss minimization at the coupling with the light guide the fibers are preferentially brought together tightly and the space in between the core is minimized. For this reason, the fibers are stripped of the cladding at the bundle end. To allow for stress distribution as the fibers are bent from the jacket covered portion to the tip, the stripped portion can be in the range of 0.5 to 4 inches. Since for each fiber the length of the portion between the ring 43 and the fiber support plate is variable, the jacketed portion that corresponds to this length is also correspondingly variable and such so that the and of the jacketed portion is preferentially at the same height from the fiber support plate and at the proximity of the top of the ring 43. The remaining length from the top of the ring to the receiving end 42 is preferentially equal for each fiber.

At the receiving end the fibers are kept together with a tube, extending from the receiving end to the proximity of ring 43 with such size as to minimize the space between the fiber cores. The tube can be cylindrical, cylindrical with flared edges, conical, or of a manifold shape that reduces the diameter from the bottom to the top and provide for the distribution of stresses as the fibers are brought together, from being apart from each other due to the separation by the jacket the reaches the top of the ring, to the tight fit in the tube. Ideally the fibers are fused together to eliminate the empty space between them.

If the fibers are not fused, the space between the fibers in the tube is filled with an optically clear material. This material provides for mechanical fixation and disallows for empty space between the fibers that can trap contamination. Additionally or alternatively, a transparent window can be placed on the top of the bundle.

The light transporting element bundle can include an additional fiber 44 (FIG. 4) coupled to a detector 45 that detects the output level and sends a signal to the control element for output detection and stabilization.

For improved transmission the tips of the fibers can be cut with a method that provides a smooth surface, such as with a diamond wheel or a laser, and then polished.

Figure 6A:
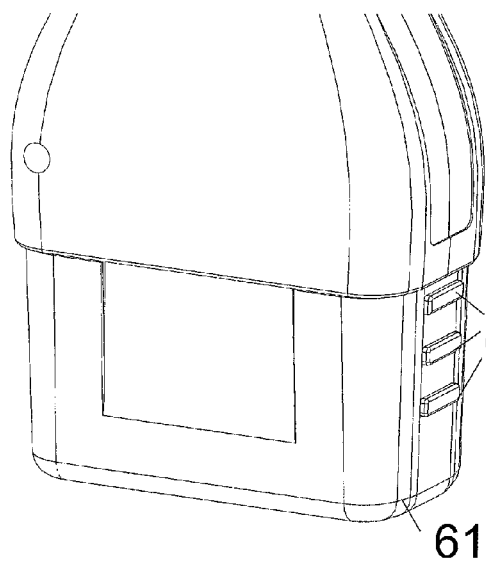
FIGS. 6a and 6b shows the protection and rinse cap, attached and removed to the body of the device.
Figure 6B:
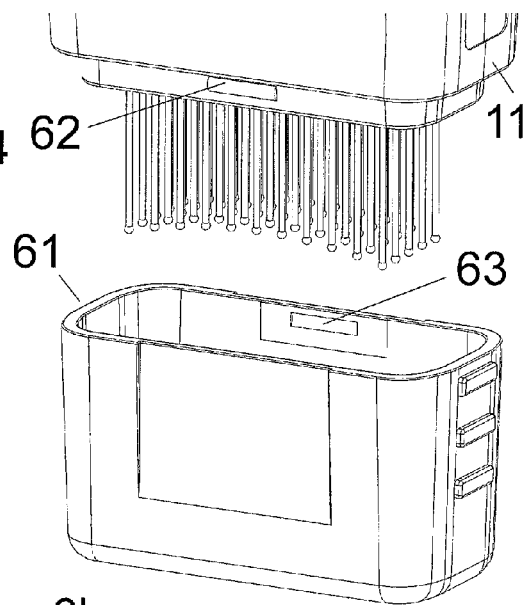

A rinse cap 61 (FIGS. 6a and 6b) can be detachably attached to the delivery end. This cap will protect the distal portion of the fibers during shipping and storage and will also serve as a rinsing container for cleaning the brush. The cap is secured on the brush by a protrusion 62 that fits into the indent 63 of the cap. The cup has ribs 64 or neural for holding. By compressing the cap at the ribs, the fit from the protrusion 62 to the indent 63 is relaxed and the cup is easily removable.

Figure 9:
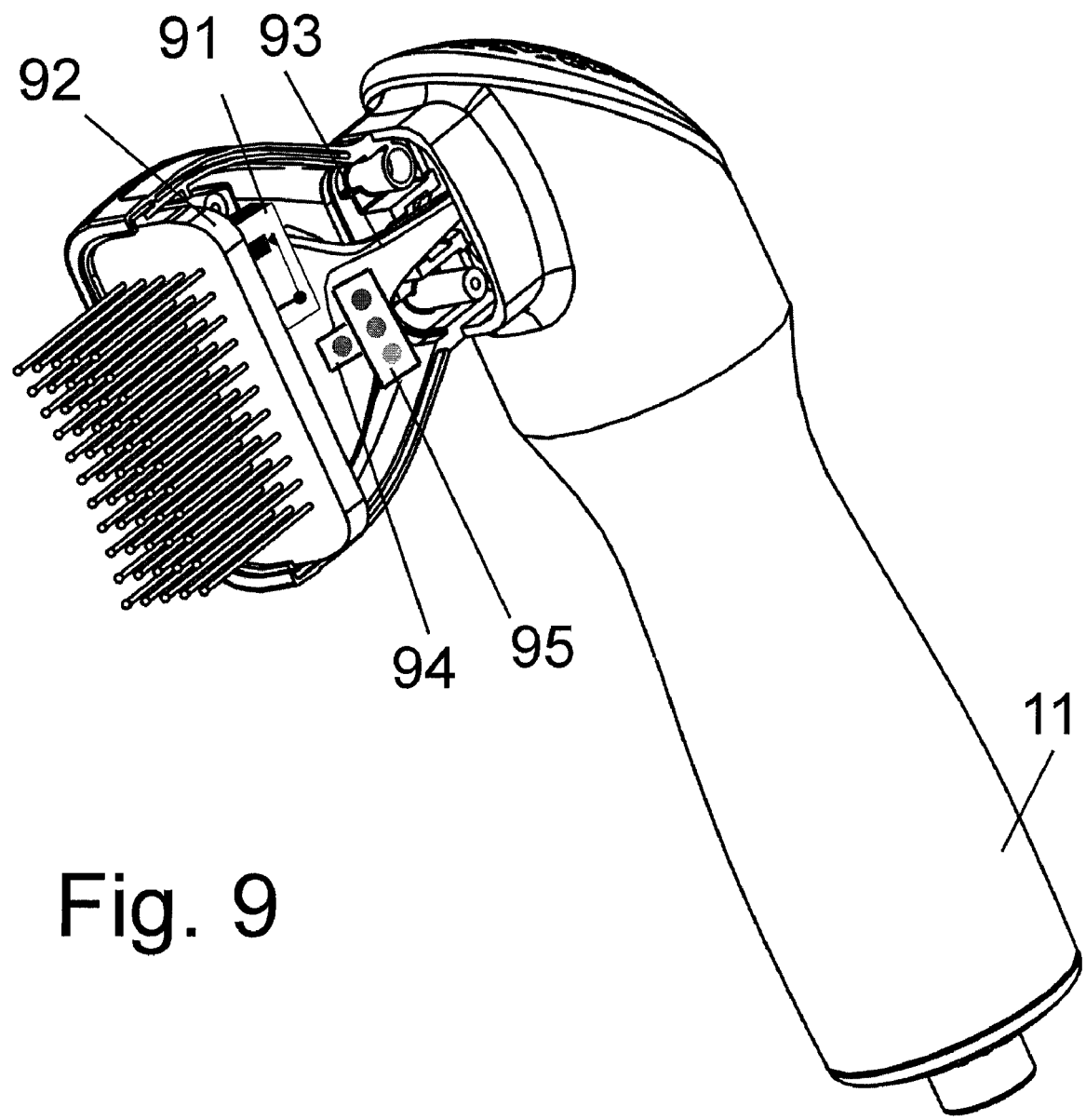
FIG. 9 shows a detector to indicate contact with the scalp and a pigmented area on brush body that changes color with use for a visual indication of the time that the device has been used.

A detection element 91 (FIG. 9) on the plate or between the body member 11 and plate 92 detects proximity or contact of fiber distal tips to the epidermis. This detection element communicates with the control module with a wire and is used to regulate activation of the device for safety.

The light transporting element bundle can include an additional fiber 93 coupled to a portion of the body member 94 that is made out of material that changes, over time, the color with exposure to light. Proximal to this portion, on the external surface of body member can be imprinted areas of various colors 95, resembling the colors of the material at different stages of light exposure. Resemblance of the color of said material to a certain imprinted color will indicate the end of the useful lifetime of the device. Such color changing materials are diazo resins such as the polymethylene para-diazo diphylamine sulfate. The exterior portion of the material can be protected from changing light due to exposure of ambient light by a coating that is clear in the visible area and blocks light in the photosensitive spectrum. Alternatively it can be covered by a retractable cover that allows viewing only when the color of said material is evaluated.

A different cap 71 (FIG. 7) of similar material to cap 61 can be detachably attached to the Fiberoptic Brush side. This cap will have at the bottom a light diffusing plate 72 to diffuse and homogenize the light for treatment of areas that are not covered by hair. The cap is secured on the brush in a manner similar to the rinse cap 61. Different size and shape diffuser plates 72a, 72b can provide various profiles 73, 74 for treatment of specific areas and lesions. The profiles can be selected so that they match the size and shape of the lesions. Alternatively, cap 71 can have no diffusing elements but openings of various shapes and sizes, acting as a distance gage and allowing the light exiting from each fiber to blend and produce uniform field.

Figure 8A:
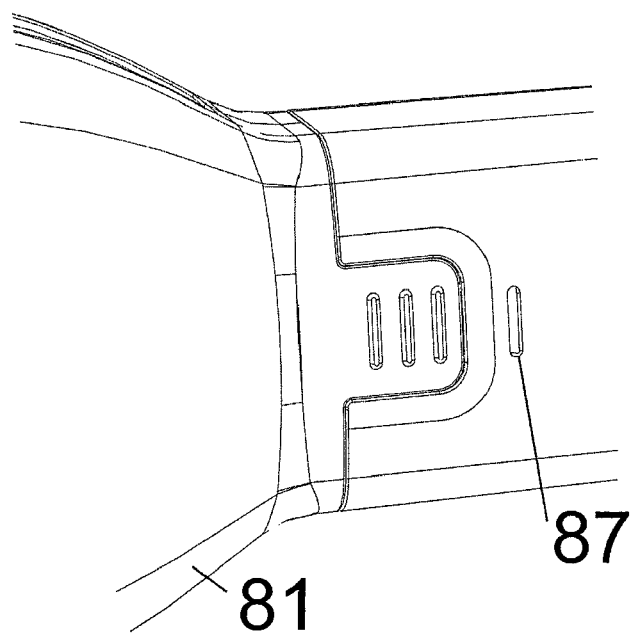
FIGS. 8a and 8b show the connector configuration for a detachable brush attached and removed from the body of the device.
Figure 8B:
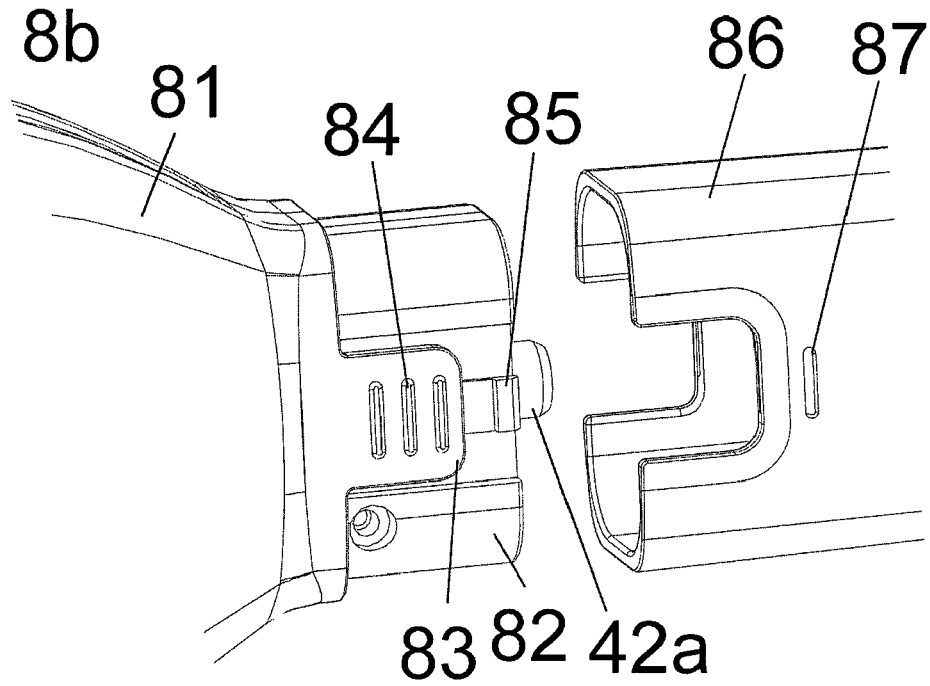

The embodiment shown in FIG. 1 is for the fiberoptic brush portion attached permanently to the light source portion of the device. Alternatively the fiberoptic brush portion can be detachably attached to the light source portion of the device with a coupling. This coupling can consist, on body to the detachable brush portion, of a protrusion 82 (FIGS. 8a and 8b) that has lips 83 with indentations 84 and extrusion 85 for snapping onto a coupler 86 that has appropriate shape to fit the Fiberoptic Brush body protrusion with an indent 87 for locking the protrusion of the coupling to the body portion of the device minus the brush. The coupling cap and protrusion can be formed of a molded resinous material, such as plastic, rubber, and the like. Other light delivery attachments can be outfitted to treat small areas of involvement.

Figure 10:
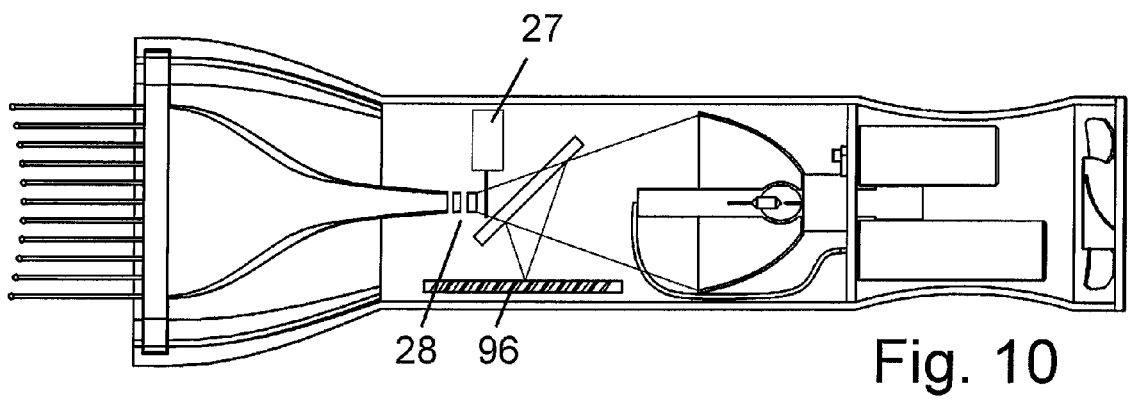
FIG. 10 shows a straight configuration (no light beam bend) of the device.

The configuration that is shown in FIG. 1 provides for a device that has the axis of the optics and the axis of the fiber bundle at an angle. Alternatively the axis of the optics and the axis of the bundle can coincide as shown in FIG. 10. The weight distribution and handling may be preferred by some users.

The therapeutic device described above can be easily used to treat inflammatory dermatoses affecting body regions covered by hair, such as the scalp. Fibers can be positioned so that the distal tips are pressed gently through such encumbrances to contact the scalp during use. The blunting or rounding of distal tips helps prevent development of the Auspitz sign during normal use. This device overcomes limitations and provides improvements over existing devices for the treatment of areas of the skin, such as the scalp, and the affected skin areas may be treated without exposing the entire body to 8-MOP and/or to UV light.

Preferred embodiments of the method of treating an inflammatory dermatosis using the aforementioned device are as follows.

For UV-B phototherapeutic treatment, simple application while gently combing through the hair for prescribed times necessary is acceptable, beginning with approximately one minimum erythema dose (MED) during the first treatment. Subsequent treatment times would increase if needed and as tolerated by the skin.

Natural skin oils, water, or light lubricants applied to the scalp may beneficially modify the optics of psoriatic skin, further reduce trauma, and provide good index matching to silica fibers. The delivery of UV radiation into the skin via direct contact with a UV-transmitting optical fiber is more efficient than through air, due to refractive index mismatching between the skin ($n_d$=1.55) and air ($n_d$=1.00). By directly contacting the scalp with the preferred fiber optic core material, fused silica ($n_d$=1.46), specular reflection at the scalp surface is greatly reduced, especially when a lubricant or topical application of psoralen-containing solution is present. The amount of such specular reflection varies mainly with the square of the difference in psoriasis, there is poor formation of the outermost skin layer. Thus, coupling of UV light into the psoriasis skin is much more efficient with direct contact between the fiber optic source and skin, in the presence of a lubricant or topical solution.

Of course, other areas of the skin such as the nails could also be treated as described above.

CLINICAL EXAMPLES

The following describes the clinical use of a phototherapy device and methods of the type described above.

Figure 11:
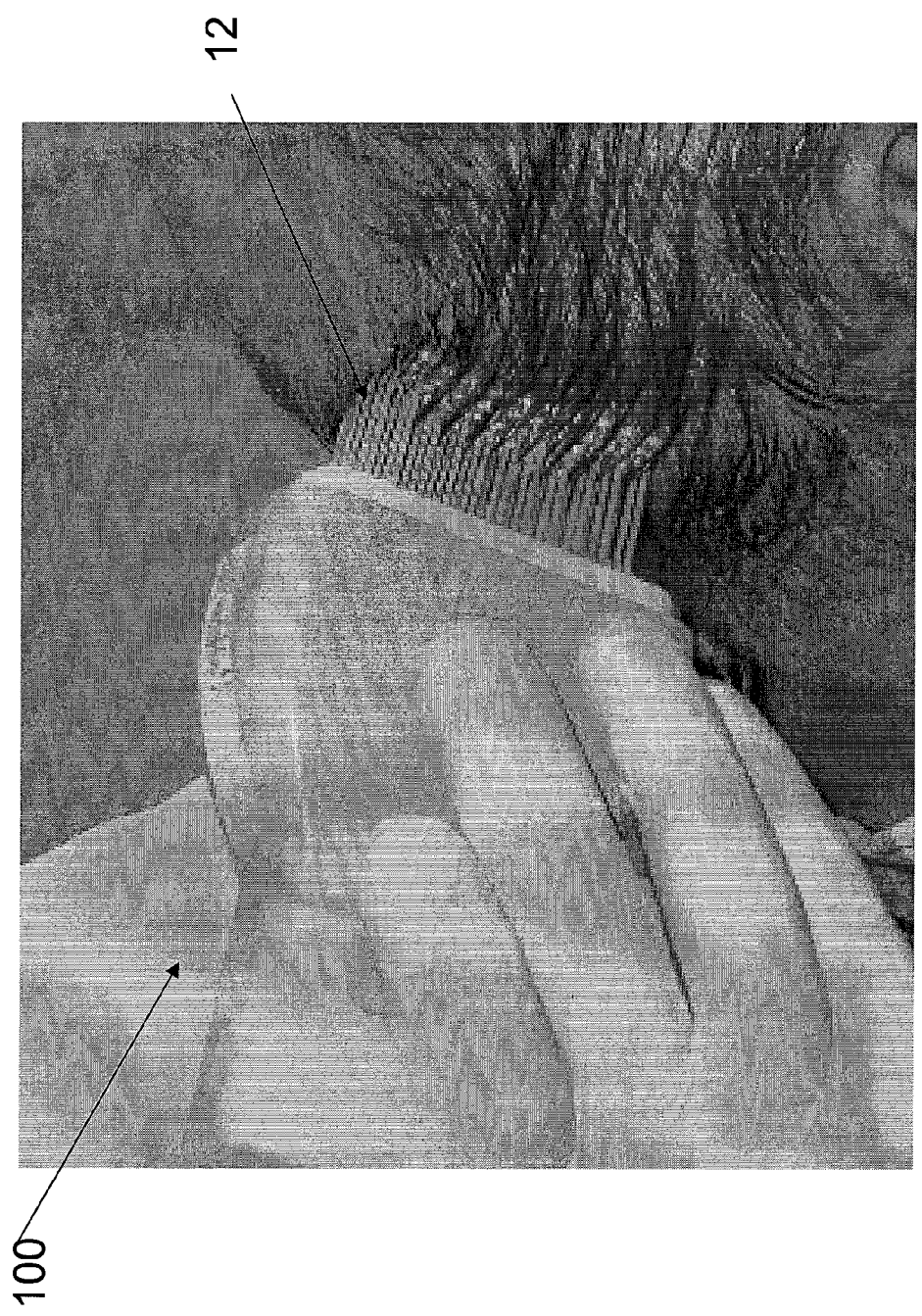
FIG. 11 is a photograph of an exemplary phototherapy device in clinical use.

As shown in FIG. 11, the scalps of patients were treated with a fiberoptic brush phototherapy device 100 of the type described above. The bristles of the brush consisted of optical fibers 12 allowing combing to deliver light to the scalp. Without this delivery system hair would absorb light and prevent it from reaching the scalp. Mineral oil was applied as in the spot treatment. Exposure levels were similar to those noted above for non-scalp areas. The phototherapy device produced 25 mW/cm2 at fall output. The output level was varied to allow delivery of the appropriate dose. FIG. 12 shows a table of exemplary dosages for various classifications of skin type, as will be understood by those skilled in the art.

As illustrated in FIG. 13, in patients with a full head of hair, the scalp was divided into five zones A, B, C, D, and E. The zones were treated for time intervals that ranged from thirty seconds to four minutes. The treatment time for the entire scalp reached a maximum of fifteen minutes. For patients with skin Type II, as is know in the art, the initial dose was set at 2 MEDs and was increased by 15-20% on each treatment. The hair was parted at that area with the fingers. If the patient complained of burning sensation discomfort, the dose was not increased or the increase was moderated. The same applied on the few occasions the patient skipped a treatment.

Patients were treated twice a week for a total of twelve treatments. If spots cleared earlier, treatment was discontinued when there was no visible lesion or hyperpigmentation on the skin. Considering that some patients missed a treatment now and then, the total time was 7-8 weeks. For the scalp preservation treatment was given once per week or every other week.

Patient 1 was a Caucasian male, 35 years old with skin type: III. His medical history included: stable psoriatic plaques on the scalp last 5 years. Previous treatment involved emollients, steroid creams, peanut oil, and tar shampoos. No topical (or systemic) treatments were given for 4 weeks prior to targeted UVB therapy. The patient's treatment occurred two times a week for a total of twelve treatments. The scalp was treated with a fiberoptic brush phototherapy device of the type described above. For the scalp, the initial dose was 180 mJ/cm$^2$ and was increased by 15-20% on each treatment until it reached 950 mJ/cm$^2$. On the scalp, clearance was achieved with 8 treatments. Preservation treatment was continued once a week for 6 weeks. The patient was clear on the last examination, 4 weeks after the last treatment.

Patient 2 was a Caucasian male, 27 years old with skin type II. His medical history included: stable psoriatic plaques on head, arms, legs and body. Previous treatment involved emollients, tar shampoos, occasional steroid creams, and various herbal therapies. No topical or systemic treatments were provided for 4 weeks prior to targeted UVB therapy. The scalp was treated with a fiberoptic brush phototherapy device of the type described above. Patient 2's treatment was similar to patient 1 but cleared faster and treatment was discontinued. The patient cleared after 6 weeks of treatment (ten treatments) and treatment was interrupted once he was clear. Preservation treatment was not given. The patient was clear on the last examination, 8 weeks after treatment.

Patient 3 was a Caucasian male, 52 years old with skin type II. His medical history included: stable psoriatic plaques on the scalp. Previous treatment involved emollients, steroid creams, and tar shampoos. No topical (or systemic) treatments were given for 4 weeks prior to targeted UVB therapy. Treatment was provided two times a week for a total of twelve treatments. The scalp was treated with a fiberoptic brush phototherapy device of the type described above. For the scalp, the initial dose was 150 mJ/cm$^2$ (about 2 MEDs) and was increased by 15-20% on each treatment until it reached 750 mJ/cm$^2$. On the scalp, clearance was achieved with 8 treatments. Preservation treatment was continued once a week. The patient was delighted with the results.

In the above examples Psoriatic lesions began to resolve after 3-4 treatments and the majority of the lesions cleared within 8-10 treatments. Tanning was observed in the treated areas. The patients were evaluated monthly following phototherapy.

Use of a fiberoptic brush type phototherapy device of the type described above resulted in successful treatment of scalp psoriasis. It was easy for the operator to perform and well tolerated by the patient. Each session was less than 15 minutes.

One or more or any part thereof of the control, sensing, or other techniques described above can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The technique can also be implemented as a computer-readable storage medium, configured with a computer program, where the storage medium so configured causes a computer to operate in a specific and predefined manner to perform the functions described herein.

As used herein the terms "light," "optics," "optical," etc are to be understood to include electromagnetic radiation both within and outside of the visible spectrum, including, for example, ultraviolet radiation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A phototherapy apparatus comprising:
   a handpiece comprising a body member and a grip;
   a plurality of elongated light transmitting elements, wherein the light transmitting elements each comprise an optical fiber, each of said elements extending between a proximal end enclosed within the body member and a distal end located outside of and distal to the body member;
   an ultraviolet light source;
   a light collection element; and
   one or more optical coupling elements;
   wherein the proximal ends of the light transmitting elements are located in close proximity to each other and comprise a fiber bundle, said bundle having an entrance face comprised of the tips of the proximal ends, and wherein the fibers of the fiber bundle are fused in proximity to the entrance face,
   wherein the light collection element is configured to collect at least a portion of the light emitted from the light source,
   wherein the one or more optical coupling elements are configured to direct at least a portion of the collected light to the entrance face comprised of the tips of the proximal ends of the light transmitting elements to couple at least portion of the collected light into the light transmitting elements,
   wherein light coupled into each of the light transmitting elements is transmitted along the element and emitted from the distal end.

2. The apparatus of claim 1 wherein the light transmitting elements are detachably affixed to the body member.

3. The apparatus of claim 2, further comprising:
   a support plate adapted to be detachably received by the body member and to support the elongated light transmitting elements;
   wherein each of the elongated light transmitting elements extend through the support element from a side of the support element proximal the body member to a side of the support element distal the body member.

4. The apparatus of claim 1, wherein the proximal ends of the light transmitting elements comprise a linear array of fibers, said array having an entrance face comprised of the tips of the proximal ends;
   wherein the one or more optical coupling elements are configured to direct light to the entrance face.

5. The apparatus of claim 4, comprising a cylindrical lens disposed in front of the entrance face of the linear array of fibers and configured to concentrate light directed to the proximal ends of the light transmitting elements onto the entrance face.

6. The apparatus of claim 1, further comprising a plurality of light concentrating elements disposed in front of the entrance face of the fiber bundle, said concentrating elements configured to concentrate light directed to the proximal ends of the light transmitting elements onto the entrance face.

7. The apparatus of claim 1, wherein the light collecting element comprises one of the group of: an ellipsoidal reflector, a parabolic reflector.

8. The apparatus of claim 7, wherein the reflector comprises a wavelength selective coating adapted to reflect radiation with wavelengths within a desired range and transmit radiation with wavelengths within a desired range, said desired range being within the ultraviolet range.

9. The apparatus of claim 1, comprising one or more filter elements configured to filter out at least a portion of the light from the source having undesired wavelengths.

10. The apparatus of claim 9, wherein the filter element comprises a dichroic mirror positioned to direct at least a portion of the collected light having undesired wavelengths away from the proximal ends of the light transmitting elements.

11. The apparatus of claim 1, wherein the one or more optical coupling elements comprise a lens configured to focus light from the light collecting element to the proximal ends of the light transmitting elements.

12. The apparatus of claim 1, further comprising one or more shutters adapted to selectively block light directed to the proximal ends of the light transmitting elements.

13. The apparatus of claim 1, wherein the portion of light coupled into the light transmitting elements comprises substantially only ultraviolet light.

14. The apparatus of claim 13, wherein the portion of light coupled into the light transmitting elements has a spectral range within the range of 280 nm to 320 nm.

15. The apparatus of claim 14, wherein the portion of light coupled into the light transmitting elements has a spectral range within the range of 308 nm to 320 nm.

16. The apparatus of claim 13, wherein the portion of light coupled into the light transmitting elements has a spectral range within the range of 320 nm to 380 nm.

17. The apparatus of claim 1, wherein the light source comprises at least one of the group of: a lamp, a laser, an excimer laser, a diode laser, a light emitting diode, an excimer gas discharge lamp.

18. The apparatus of claim 1, wherein the distal ends of the light transmitting elements are arranged in an array.

19. The apparatus of claim 18, wherein the array is a two dimensional array.

20. The apparatus of claim 18 wherein tips of the distal ends of the light transmitting elements are located at positions in space having a locus characterized by a curved surface or arc.

21. The apparatus of claim 20 wherein the curved surface or arc comprises one of the group of: a circular arc, a parabolic arc, and ellipsoidal arc, a cylindrical segment, a spherical segment, a toroidal segment.

22. The apparatus of claim 20, wherein the curved surface or arc has an associated radius or radii of curvature within the range of about 2 inched to about 6 inches.

23. The apparatus of claim 20 wherein the locus is adapted to substantially conform to the shape of a human scalp.

24. The apparatus of claim 18, wherein the array is arranged to provide substantially uniform fluence of light emitted from the distal ends of the light transmission elements at an area of a treatment surface.

25. The apparatus of claim 1, wherein the distal end of one or more of the light transmitting elements comprises a bulbous tip comprised of a light emitting spherical segment.

26. The apparatus of claim 25, wherein the spherical segment has a radius of curvature within the range of about 0.25 mm to about 3.0 mm.

27. The apparatus of claim 1, wherein the distal end of one or more of the light transmitting elements comprises a rounded tip.

28. The apparatus of claim 27, wherein the rounded tip has a radius of curvature within the range of about 0.25 mm to about 3.0 mm.

29. The apparatus of claim 1, wherein the fiber comprises an inner core surrounded by an outer cladding, said inner core having a radius within the range of about 0.1 mm to about 3 mm.

30. The apparatus of claim 3, wherein the light transmitting elements and support plate are autoclavable.

31. The apparatus of claim 1, further comprising
a control unit in communication with one or more of: the light source, collecting element, or the one or more optical coupling elements,
wherein the control unit configured to selectively adjust the duration or intensity of light emitted from the distal ends of the light transmitting elements.

32. The apparatus of claim 31, wherein
the control unit is in communication with a power supply, and
said control unit configured to control the power supplied to the light source to adjust the duration or intensity of light coupled into the light transmitting elements.

33. The apparatus of claim 31, further comprising a dosimetry sensor adapted to, during operation, provide to the control unit information indicative of a dose of treatment light directed from the light transmitting elements to a treatment surface.

34. The apparatus of claim 33, wherein the control unit is configured to selectively adjust the duration or intensity of light coupled into the light transmitting elements based on said information.

35. The apparatus of claim 32 further comprising the power supply, wherein the power supply is enclosed within the body element.

36. The apparatus of claim 1, wherein the body element is substantially opaque to ultraviolet light.

37. The apparatus of claim 31, further comprising a sensor adapted to sense the proximity or contact of the distal end of one or more of the elongated light transmitting elements to a treatment surface, wherein the sensor is in communication with the control unit, and said control unit is configured to inhibit emission of light from the source when said sensor does not indicate proximity or contact of the distal end of one or more of the elongated light transmitting elements to the treatment surface.

38. A method of treating an area of skin affected by inflammatory skin disease comprising:
providing an effective dose of treatment light to the affected area from a phototherapy device, said phototherapy device comprising:
a handpiece comprising
a body member and a grip;
a plurality of elongated light transmitting elements, wherein the light transmitting elements each comprise an optical fiber, each of said elements extending between a proximal end enclosed within the body member and a distal end located outside of and distal to the body member;
a light source;
a light collection element; and
one or more optical coupling elements;
wherein the proximal ends of the light transmitting elements are located in close proximity to each other, and comprise a fiber bundle, said bundle having an entrance face comprised of the tips of the proximal ends, and wherein the fibers of the fiber bundle are fused in proximity to the entrance face,
wherein the light collection element is configured to collect at least a portion of the light emitted from the light source,
wherein the one or more optical coupling elements are configured to direct at least a portion of the collected light to the entrance face of the proximal ends of the light transmitting elements to couple at least portion of the collected light into the light transmitting elements, wherein light coupled into each of the light transmitting elements is transmitted along the element and emitted from the distal end.

39. The method of claim 38, wherein the treatment light comprises ultraviolet light.

40. The method of claim 39 wherein providing treatment light comprises bringing the distal ends of the light transmitting elements into proximity or contact with the affected area.

41. The method of claim 40, wherein the providing treatment light comprises, while maintaining distal ends of the light transmitting elements into proximity or contact with the affected area, moving the distal ends across the affected area to provide at least one minimal erythema dose of treatment light to substantially the entire the affected area.

42. The method of claim 41 wherein at least a portion of the affected area is a hair bearing region, and moving the distal ends across the affected area comprises combing the distal ends through the hair.

* * * * *